(12) United States Patent
Fuchs et al.

(10) Patent No.: US 7,939,262 B2
(45) Date of Patent: May 10, 2011

(54) METHOD FOR THE DIAGNOSIS OF SCHIZOPHRENIA

(75) Inventors: Sara Fuchs, Rehovot (IL); Tal Ilani, Kiryat-Ono (IL); Orly Perl, Kiryat-Ono (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 12/490,195

(22) Filed: Jun. 23, 2009

(65) Prior Publication Data

US 2010/0041043 A1    Feb. 18, 2010

(30) Foreign Application Priority Data

Aug. 15, 2000 (IL) .......................................... 137865

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.5

(58) Field of Classification Search ........................ None
See application file for complete search history.

(56) References Cited

OTHER PUBLICATIONS

Boneberg et al. D3 dopamine receptor mRNA is elevated in T cells of schizophrenic patients wehreas D4 dopamine receptor mRNA is reduced in CD4+-T cells. Journal of Neuroimmunology, vol. 173, pp. 180-187, 2006.*
Burghaus et al, ".Quantitative assessment of nicotinic acetylcholine receptor proteins in the cerebral cortex of Alzheimer patients", Mol Brain Res 76:385-388 (2000).
Court et al, "Neuronal Nicotinic Receptors in Dementia with Lewy Bodies and Schizophrenia: α-Bungarotoxin and Nicotine Binding in the Thalamus", J Neurochem 73(4):1590-1597 (1999).
Creese et al, Dopamine Receptor Binding Predicts Clinical and pharmacological Potencies of Antischizophrenic Drugs. Science 192:481 (1976).
Freedman et al, "The α7-nicotinic acetylcholine receptor and the pathology of hippocampal interneurons in schizophrenia", J Chem. Neuroanat 20: 299-306 (2000).
Guan et al, "Decreased protein level of nicotinic receptor α7 subunit in the frontal cortex from schizophrenic brain", Neuroreport 10:1779-1782 (1999).
Guan et al, "Decreased Protein Levels of Nicotinic Receptor Subunits in the Hippocampus and Temporal Cortex of Patients with Alzheimer's Disease", Neurochem 74:237-243 (2000).
Hellstrom-Lindahl et al, "Expression of nicotinic receptor subunit mRNAs in lymphocytes from normal and patients with Alzheimer's disease", Alz Research 3:29-36 (1997).
Hellstrom-Lindahl et al, "Regional distribution of nicotinic receptor subunit mRNAs in human brain: comparison between Alzheimer and normal brain", Mol Brain Res 66:94-103 (1999).
Hietala et al, "Dopamine in Schizophrenia", Ann Med 28:557 (1996).

Ilani et al, "A peripheral marker for schizophrenia: Increased levels of D3 dopamine receptor mRNA in blood lymphocytes", Proc Natl Acad Sci USA 98(2):625-628 (2001).
Kwak et al, "Change of dopamine receptor mRNA expression in lymphocyte of schizophrenic patients", BMC Med Genet 2(1):3 (2001).
Leonard et al, "Smoking and schizophrenia: abnormal nicotinic receptor expression", Eur J Pharmacol 393:237-242 (2000).
Levant B, "The D3 Dopamine Receptor: Neurobiology and Potential Clinical Relevance", Pharmacol Rev 49:231 (1997).
Nagai et al, "Decrease of the D3 dopamine receptor mRNA expression in lymphocytes from patients with Parkinson's disease", Neurology 46:791-795 (1996).
Ricci et al, "Dopamine D4 receptor in human peripheral blood lymphocytes: a radioligand binding assay study." Neurosci Lett 229:130-134 (1997).
Seeman et al, "Dopamine receptors and transporters in Parkinson's disease and schizophrenia", FASEB J 4:2737-2744 (1990).
Takahashi et al, "Human peripheral blood lymphocytes express D5 dopamine receptor gene and transcribe the two pseudogenes", FEBS Lett 314:23-25 (1992).
Wang et al, "β-Amyloid (1-42) Binds to α-7 Nicotinic Acetylcholine Receptor with High Affinity: Implications for Alzheimer's Disease Pathology", J Biol Chem 275 (8):5626-5632 (2000).
Willner P, "The dopamine hypothesis of schizophrenia: current status, future prospects", Int Clin Psychopharmacol 12:297-308 (1997).
Myers RH., "Huntington's disease genetics" NeuroRx. vol. 1, No. 2, pp. 255-262 (2004).
Farlow MR., "Etiology and pathogenesis of Alzheimer's disease" Am J Health Syst Pharm. vol. 55, Supplement 2, pp. 55-10 (1998).
Vogel et al., "Decreased levels of dopamine D3 receptor mRNA in schizophrenic and bipolar patients" Neuropsychobiology. vol. 50, No. 4, pp. 305-310 (2004).
Czermak et al., "Reduced dopamine 03 receptor expression in blood lymphocytes of smokers is negatively correlated with daily number of smoked cigarettes: a peripheral correlate of dopaminergic alterations in smokers" Nicotine Tob Res. 6(1 ):49-54 (2004).
Chu et al. "Increased alpha 7 nicotinic acetylcholine receptor protein levels in Alzheimer's disease patients". Dement Geriatr Cogn Disord. vol. 19, Nos. 2-3, pp. 106-112,2005. Epub (2004).
Kroese et al., "Genetic tests and their evaluation: can we answer the key questions?" Genet Med. vol. 6, No. 6, pp. 475-480 (2004).
Lucentini et al., "Gene Association Studies Typically Wrong" The Scientist. vol. 18, No. 24, pp. 20 (pp. 1/5-5/5) (2004).
Ilani et al., "A peripheral marker for schizophrenia: 03 dopamine receptor on blood lymphocytes" Society for Neuroscience Abstracts, vol. 26, No. 1-2, Abstract 112.10, 2000. Available on CO-ROM on Oct. 20, 2000 and in print on Sep. 1, 2000.

(Continued)

*Primary Examiner* — Jennifer Dunston
(74) *Attorney, Agent, or Firm* — Browdy and Neimark, PLLC

(57) ABSTRACT

A method for the diagnosis of schizophrenia in an individual comprises: (i) measuring mRNA of either D3 dopamine receptor or α7 nicotinic acetylcholine receptor (α7 AChR), and of a control gene in peripheral blood lymphocytes (PBLs) of the individual and of at least one healthy control individual; (ii) calculating the ratio between the receptor mRNA and the control gene mRNA for each individual; and (iii) evaluating the ratio between the ratios obtained in (ii) for the tested individual and for the at least one healthy control individual, wherein (a) an increase in the D3 dopamine receptor mRNA or a decrease in the α7 AChR in the tested individual in comparison to healthy individuals, indicates that said tested individual has a higher likelihood of having schizophrenia than the healthy controls.

10 Claims, 4 Drawing Sheets

OTHER PUBLICATIONS

Schmittgen et al., "Quantitative reverse transcription-polymerase chain reaction to study mRNA decay: comparison of endpoint and real-time methods" Anal Biochem. vol. 285, No. 2, pp. 194-204 (2000).

Van der Weide et al., "D3 dopamine receptor mRNA expression in lymphocytes: a perimpheral marker for schizophrenia?" Acta Neuropsychiatra, vol. 15, pp. 91-93 (2003).

Perl et al., "Low levels of alpha7-nicotinic acetylcholine receptormRNA on peripheral blood lymphocytes in schizophrenia and its association with illness severity" Neuropsychology, vol. 53, pp. 88-93 (2006).

Geddes et al., "Schizophrenic subjects with no history of admission to the hospital" Psychological Medicine. vol. 25, pp. 859-868 (1995).

* cited by examiner

HL16, HL15, HL14, SP1, SP2, SP3

β-actin

α7 AChR

SEQUENCE LISTING

```
<160> NUMBER OF SEQ ID NOS: 8

<210> SEQ ID NO 1
<211> LENGTH: 25
<212> TYPE: DNA
<213> ORGANISM: HUMAN

<400> SEQUENCE: 1
ggagacggaa aaggatcctc actcg                                         25

<210> SEQ ID NO 2
<211> LENGTH: 26
<212> TYPE: DNA
<213> ORGANISM: HUMAN

<400> SEQUENCE: 2
tcagcaagac aggatcttga ggaagg                                        26

<210> SEQ ID NO 3
<211> LENGTH: 24
<212> TYPE: DNA
<213> ORGANISM: HUMAN
```

-continued

```
<400> SEQUENCE: 3
cgggatccca ccccagactc cacc                                              24

<210> SEQ ID NO 4
<211> LENGTH: 24
<212> TYPE: DNA
<213> ORGANISM: HUMAN

<400> SEQUENCE: 4
cggaattccg ttgcggaact cggc                                              24

<210> SEQ ID NO 5
<211> LENGTH: 22
<212> TYPE: DNA
<213> ORGANISM: HUMAN

<400> SEQUENCE: 5
aagtttgggt cctggtctta cg                                                22

<210> SEQ ID NO 6
<211> LENGTH: 21
<212> TYPE: DNA
<213> ORGANISM: HUMAN

<400> SEQUENCE: 6
gatcatggtg ctggcgaagt a                                                 21

<210> SEQ ID NO 7
<211> LENGTH: 22
<212> TYPE: DNA
<213> ORGANISM: HUMAN

<400> SEQUENCE: 7
tgaagtgtga cgtggacatc cg                                                22

<210> SEQ ID NO 8
<211> LENGTH: 22
<212> TYPE: DNA
<213> ORGANISM: HUMAN

<400> SEQUENCE: 8
gctgtcacct tcaccgttcc ag                                                22
```

METHOD FOR THE DIAGNOSIS OF SCHIZOPHRENIA

FIELD OF THE INVENTION

The present invention relates to methods for the diagnosis and follow-up of schizophrenia and other mental and neurodegenerative disorders, and kits for use in said methods.

BACKGROUND OF THE INVENTION

Schizophrenia is a neuropsychiatric disorder afflicting about one percent of the population. It is characterized by delusions, hallucinations, disorders in organizing thoughts logically, and emotional withdrawal. There is a well-known tendency for schizophrenia to run in families.

Although the exact pathogenesis of schizophrenia is still not known precisely, a common belief is that excessive activity at dopaminergic synapses in the brain plays a prominent role. To date, a definitive diagnosis of schizophrenia requires a 6-month duration of symptomotology, and relies on heterogeneous symptoms. Because there is neither an effective biological marker for identifying schizophrenia (Willner, 1997; Hietala and Syvalahti, 1996), nor an accurate and rapid diagnosis to ensure more optimal management at an early stage in the illness, there remains a vital need for a convenient assay for diagnosis and follow-up of schizophrenia.

Most of the drugs used to treat schizophrenia act to control the symptoms by neuroreceptor antagonism. Moreover, the dopaminergic basis of schizophrenia is strongly supported by the close correlation between clinical efficacy of antipsychotic medications and their potency to antagonize the binding of dopamine to its receptors (Creese et al., 1976).

Dopamine receptors are divided into two subclasses D1 and D2. The D1 subclass contains the $D_1$ and $D_5$ receptor subtypes, and the D2 subclass contains the $D_2$, $D_3$ and $D_4$ subtypes (Levant, 1997). The dopamine hypothesis of schizophrenia relates specifically to the D2 subclass. Notably, most drugs effective in treating schizophrenia exhibit D2 receptor antagonistic activity, and administration of a selective D1-like antagonist has been reported to result in the worsening of symptoms (Karlsson et al., 1995). Among the receptors in the D2 subclass ($D_2$, $D_3$ and $D_4$), the $D_3$ receptor is located principally in an area of the brain that could be very relevant to schizophrenia, the nucleus accumbens (Willner, 1997). Studies with positron-emission tomography and postmortem brain tissue have indicated increased levels of D2-like dopamine receptors in schizophrenics when compared with nonschizophrenic patients (Seeman and Niznik, 1990). Thus, the level of dopamine receptor could be employed as a marker for schizophrenia if it could be analyzed on an available tissue, preferably a peripheral one.

High affinity binding of dopaminergic ligands, as well as the presence of mRNA of several dopamine receptor subtypes ($D_3$, $D_4$ and $D_5$) in human peripheral blood lymphocytes (PBLs) have been reported in recent years (Ricci et al., 1997, Takahashi et al., 1992). It should be noted, however, that neither $D_2$ nor $D_1$ dopamine receptor subtypes, which are the most abundant receptors in the brain and belong to the D2 and the D1 subclasses, respectively, have been detected in lymphocytes. Although the significance of dopamine receptors, as well as of other neurotransmitter receptors, in lymphocytes is still not clear, it has been suggested that they may reflect corresponding brain receptors. Several studies have demonstrated the increased binding of dopamine antagonists in lymphocytes of schizophrenic patients as compared with healthy individuals (Bondy et al., 1984; Bondy et al., 1985). In addition, a previous study carried out in the laboratory of the present inventors has demonstrated that spiperone (a D2 antagonist) binding in peripheral blood lymphocytes is higher in neuroleptic responders as compared with treatment-resistant schizophrenic patients (Grodzicki et al., 1990). However, the observed differences in binding studies were rather low and often not significant. The discrepancies obtained could have resulted from the crossreactivity of radioligands with different subtypes of the receptor and with other receptors (e.g. serotonergic), and from scattered levels of binding sites. Therefore, such binding assays in lymphocytes may not be suitable for a reliable assay for schizophrenia.

Such a correlation between the status of receptors in the brain and in PBLs has also been demonstrated in Alzheimer's disease, where muscarinic receptors are reduced in both brains and lymphocytes (Ferrero et al., 1991). A previous study by Nagai et al. (1996) demonstrated that patients with Parkinson's disease exhibit reduced levels of $D_3$ receptor mRNA in PBLs, as compared with healthy individuals. These latter findings provide another example of a disease that is associated with an insult in the central nervous system that is reflected in PBLs. This reduction has also been detected in medicated and non-medicated patients.

Central cholinergic systems were also shown to control basic functions of the brain. Acetylcholine mediates synaptic transmission in the vertebrate central nervous system through the activation of two major receptor subtypes, the muscarinic and nicotinic acetylcholine receptors (AChRs). The muscarinic receptors are G-coupled receptors, and the nicotinic receptors are ligand-gated ionic channels. Nicotinic AChRs are composed of five subunits organized around a central ion channel. Neuronal nicotinic AChRs are usually built as heteropentamers, composed of $\alpha(\alpha2-\alpha9)$, and $\beta(\beta2-\beta4)$ subunits. $\alpha7$, $\alpha8$, and $\alpha9$ can function as homomeric AChRs and are of special interest because they bind the curarinetric neurotoxin, $\alpha$-bungarotoxin. ($\alpha$-BTX$\beta$). These receptors are characterized by a rapid rate of desensitization, and a high level of selectivity to calcium.

Several recent studies have suggested that nicotinic $\alpha7$ AChR may be associated with some aspects of schizophrenia (Guan et al., 1999). Nicotine administration normalizes two psychophysiological deficits, typical for schizophrenia: disordered eye movements, and the P50 auditory evoked potential gating deficit (Olincy et al., 1998). The genes responsible for these two deficits are linked genetically to the chromosomal locus (15q14) of the $\alpha7$-nicotinic receptor gene (Leonard et al., 2000). $\alpha7$ AChR has been found to be expressed in the mammalian brain, especially throughout the hippocampus (Hellstrom-Lindahl et al., 1999), a brain region associated with schizophrenia.

Interestingly, the vast majority of schizophrenic patients are smoking. They appear to extract more nicotine than normal smokers, possibly due to different inhalation patterns (Olincy et al., 1997). This fact raised the possibility that nicotine might influence the levels of $\alpha7$ receptor. However, searching for receptor differences between smokers and non-smokers in the general population did not reveal any significant differences (Stassen et al., 2000).

Association between the $\alpha7$ nicotinic receptor levels and Alzheimer's disease has also been investigated. Decrease in the expression of $\alpha7$ AChR was observed in post mortem tissue from Alzheimer's disease patients, exhibiting a reduction of 36% in the hippocampus (Guan et al., 2000). Burghaus et. al. (2000) reported a decrease in protein amount of $\alpha7$ AChR in Alzheimer's disease cortices. Wang et. al. (2000) described an interaction of $\alpha7$ AChR and $\beta$-amyloid (1-42) as a mechanism involved in the pathophysiology of Alzheimer's disease. There have been some other conflicting reports demonstrating higher levels of the α7 AchR mRNA in the hippocampus (Hellstrom-Lindhal et al., 1999) as well as in lymphocytes (Hellstrom-Lindahl et al., 1997) of Alzheimer's disease patients, compared to healthy controls.

Freedman et al. (2000) reported that interneurons in the hippocampus and in other forebrain structures are decreased in number and function in subjects with schizophrenia. Decreased α7-nicotinic receptor immunoreactivity was found in the frontal cortex and in the nucleus reticularis thalami of schizophrenic patients (Freedman et al., 2000). Court et. al. (1999) described a reduction in the α-BTX binding, and no significant alterations in the nicotine binding in post mortem brains of schizophrenic patients. A significant decrease in the level of α7 AChR was also observed by Guan et. al. (1999) in the frontal cortex of schizophrenics when compared with controls, suggesting that α7 AChR may be involved in inhibitory neuronal pathways engaged in this disorder.

SUMMARY OF THE INVENTION

According to the present invention, we measured the mRNA levels of dopamine receptors and of α7 nicotinic acetylcholine receptor (AChR) in peripheral blood lymphocytes (PBLs) of schizophrenics and healthy individuals in order to find out if they can serve as peripheral markers for this disorder. Since the inhibitory D2 subclass of dopamine receptors is considered to be associated with neuropsychiatric disorders rather than the D1 subclass, we have focused only on the $D_3$ and $D_4$ subtypes, both belonging to the D2 subclass. We have then found a correlation between $D_3$ dopamine receptor on lymphocytes and schizophrenia, showing a significant elevation of above about 1.6, particularly 2-4, folds in mRNA level of $D_3$ but not of $D_4$, in the schizophrenic patients. In addition, a significant decrease (>20%, particularly 20-98%) of the α7 AChR mRNA levels in PBLs of schizophrenic patients was observed. The changes in the mRNA level of the $D_3$ dopamine receptor and of the α7 AChR in schizophrenic patients are not affected by different drug treatments. Moreover, non-medicated patients exhibit the same pattern, indicating that these changes are not a result of the medical treatment.

The present invention thus relates to the evaluation of the mRNA levels of $D_3$ dopamine receptor and/or of α7 AChR in PBLs of an individual as reliable peripheral markers for the identification and follow-up of schizophrenia, of other mental disorders, and of neurodegenerative disorders.

In one aspect, the invention relates to a method for the diagnosis and follow-up of a mental disorder or of a neurodegenerative disorder in an individual, comprising:

(i) measuring mRNA of $D_3$ dopamine receptor and/or of α7 AChR, and of a control gene in peripheral blood lymphocytes (PBLs) of said individual and of at least one healthy control individual;

(ii) calculating the ratio between the $D_3$ dopamine receptor mRNA and the control gene mRNA, and/or the ratio between α7 AChR mRNA and the control gene mRNA for each individual; and (iii) evaluating the ratio between the ratios obtained in (ii) for the tested individual and for the at least one healthy control individual, wherein an increase in the ratio of the $D_3$ dopamine receptor mRNA and/or a decrease in the ratio of the α7 AChR mRNA in the tested individual in comparison to healthy individuals, indicate that said tested individual has a high likelihood of having said mental disorder or neurodegenerative disorder, wherein said increase in the $D_3$ dopamine receptor mRNA and/or decrease in the α7 AchR mRNA in the tested individual is correlated to said mental disorder or neurodegenerative disorder.

The mental disorder may be, for example, schizophrenia, maniac depression, Tourette syndrome or a similar disorder, and the neurodegenerative disorder may be, for example, Parkinson's disease, Alzheimer's disease or Huntington's disease. For each disease or disorder, the mRNA of the $D_3$ dopamine receptor, and/or of the α7 AChR, and of a control gene are measured in PBLs of tested individuals suffering from said disorder, and in PBLs of healthy control individuals, the ratio between the $D_3$ dopamine receptor mRNA and the control gene mRNA, and/or the ratio between α7 AChR mRNA and the control gene mRNA for each individual is calculated, and the correlation between said increase or decrease is evaluated for each disorder or disease in the same way as described herein in detail for schizophrenia.

In one embodiment, the invention relates to a method for the diagnosis and follow up of schizophrenia in an individual, comprising:

(i) measuring mRNA of $D_3$ dopamine receptor and/or of α7 AChR and of a control gene in PBLs of said individual and of at least one healthy control individual;

(ii) calculating the ratio between the $D_3$ dopamine receptor mRNA and the control gene mRNA and/or the ratio between α7 AChR mRNA and the control gene mRNA for each individual; and (iii) evaluating the ratio between the ratios obtained in (ii) for the individual tested for schizophrenia and for the at least one healthy control individual, wherein an increase of above 1.6 fold, preferably 2-4, in the $D_3$ dopamine receptor mRNA and/or a decrease of more than 20%, preferably 20-98%, in the α7 AChR mRNA in the tested individual in comparison to healthy individuals, indicate that said tested individual has a high likelihood of having schizophrenia.

In order to carry out this assay, blood is obtained from individuals, PBLs are isolated therefrom, and total RNA is isolated from the lymphocytes by standard methods as well known in the art. The mRNA of the total RNA is then reverse-transcribed into cDNA that is used for PCR amplification using primers for the $D_3$ dopamine receptor, for the α7 AChR, and for a control house keeping gene such as β-actin, α-actin, NADH or tubulin. Measuring the $D_4$ dopamine receptor-mRNA can also serve as a control. Quantification of the PCR products by densitometry, PCR-ELISA, fluorescence techniques, or Southern blot, correlates to the mRNA levels of the $D_3$ dopamine receptor, α7 AChR, and of the control gene in the PBLs. For example, when the quantification of the PCR products is carried out by densitometry, the program, in a defined area, gives a number corresponding to the brightness intensity.

In one embodiment, the mRNA level of the $D_3$ dopamine receptor, and/or of the α7 AChR, and of a control gene of a tested individual, e.g. a schizophrenic individual, is compared with the mRNA level of the $D_3$ dopamine receptor, and/or of the α7 AChR, and of a control gene of a sole healthy individual, preferably of the same age and sex. In another embodiment, the comparison is made with a pool of PBLs of two or more healthy individuals.

In another aspect, the invention relates to a kit for use in the method of the invention. The kit comprises, for example, (i) means for isolating mRNA from PBLs; (ii) means for reverse transcription and for PCR; and (iii) means for detection of PCR products. The kit may also contain means for separating PBL from whole blood.

In one embodiment, the assay may be carried out by the use of DNA arrays or differential display.

DESCRIPTION OF PREFERRED EMBODIMENTS

Figure 1:
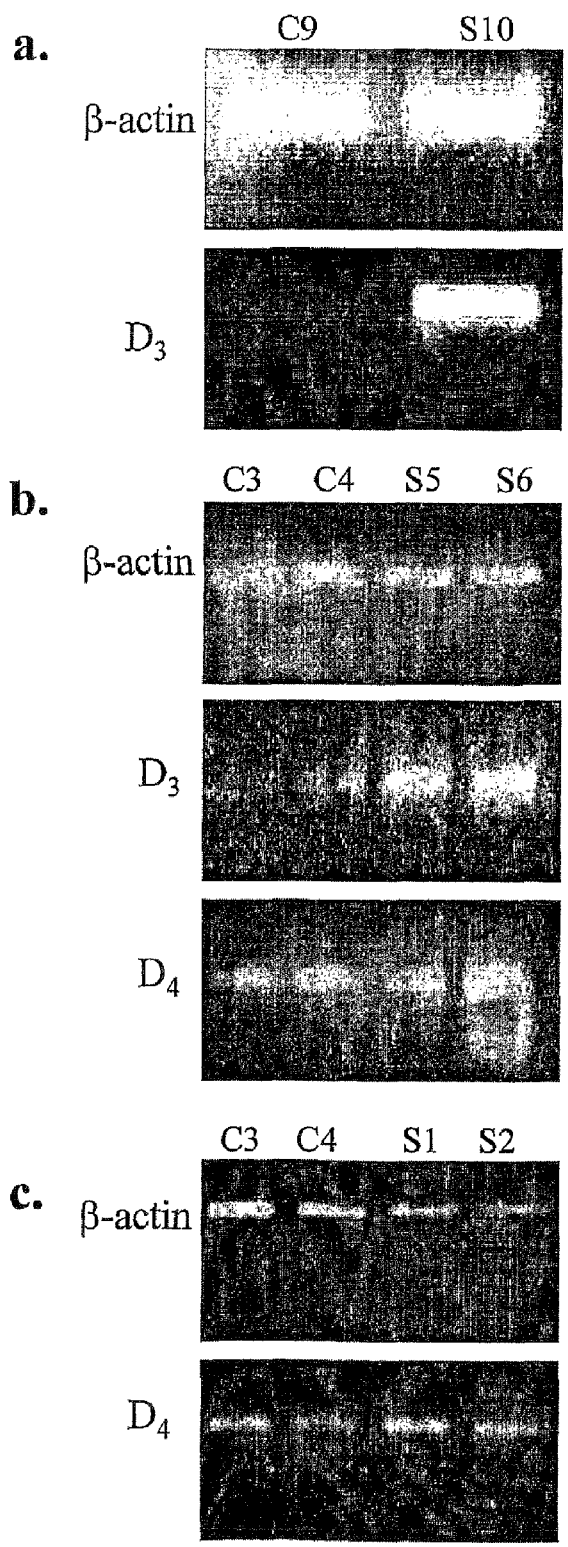
FIGS. 1a-1c shows ethidium bromide staining of $D_3$, $D_4$, and β-actin PCR products obtained from mRNA of peripheral blood lymphocytes (PBLs) of schizophrenic (S) and control healthy (C) individuals.

The invention will now be illustrated by the following non-limiting examples.

EXPERIMENTAL

Patients. Schizophrenic patients were recruited from Tyrat Hacarmel and Beer Yaacov Mental Health Centers, Israel, after providing written informed consent for participation in the study. The study has been approved by the Institutional Review Board for human studies in these two mental health centers. All patients were formally diagnosed according to the Diagnostic and Statistical Manual of Mental disorder-IV criteria and evaluated by using standard rating scales by a senior psychiatrist. Healthy individuals' age and sex matched the patient group as much as possible.

Lymphocyte isolation. Blood (40-50 ml for $D_3$ dopamine receptor, or 20-30 ml for the α7 AChR) was drawn from the cubital vein into a heparinized plastic syringe, and then transferred into a sterile 50-ml plastic tube. Blood samples were diluted with an equal volume of phosphate-buffered saline (PBS), were placed onto FICOLL-PAQUE gradients, and then were centrifuged for 30 minutes at 400×g. FICOLL-PAQUE is sterile density gradient media which is based on FICOLL PM400 (polysucrose) and sodium diatrizoate. The lymphocyte layer was collected, and washed twice in PBS. The resulting pellet was immediately frozen at −80° C. until RNA preparation.

Reverse Transcription—PCR analysis: Total RNA was isolated from lymphocytes by the guanidinum-thiocyanate method, and the amount and quality of RNA were determined by spectrophotometry and gel electrophoresis (2% agarose for the $D_3$ dopamine receptor, or 1.5% for the α7 AChR; GibcoBRL). Two μg of total RNA were reverse transcribed into first-strand cDNA using poly-dT-priming and 20 units of Molony murine leukemia virus reverse transcriptase. Two μl cDNA product (80 ng RNA) was used for the PCR amplification at a final concentration of 1×PCR buffer (Perkin-Elmer), and 1 U of Taq DNA polymerase (Perkin-Elmer) in a 25 μl final volume. PCR was carried out in a DNA thermocycler (Minicycler MJ research, MA) for 23 cycles (β-actin), 38 cycles ($D_3$ and $D_4$ dopamine receptors), and 39 cycles (α7 AChR). Annealing temperatures for β-actin, for $D_3$ and for $D_4$ dopamine receptors was 60° C., while that for α7 AChR was 57° C. The amplification was found to be linear between 30 and 40 cycles for $D_3$ and $D_4$ dopamine receptors, as well as for the α7 AChR, and between 19 and 25 cycles for β-actin.

The PCR primers for $D_3$-, $D_4$-dopamine receptors, for α7 AChR, and for β-actin were designed to include at least one intron, to eliminate amplification of genomic DNA. Their sequences were as follows:

```
                                            SEQ ID NO: 1
D3 dopamine receptor -
GGAGACGGAAAAGGATCCTCACTCG (nt 655-680);

SEQ ID NO: 2
TCAGCAAGACAGGATC TTGAGGAAGG (nt 1203-1177).

SEQ ID NO: 3
D4 dopamine receptor -
CGGGATCCCACCCCAGACTCCACC (nt 964-988);

SEQ ID NO: 4
CGGAATTCCGTTGCGGAACTCGGC (nt 1240-1216).

SEQ ID NO: 5
α7 AChR receptor-
AAGTTTGGGTCCTGGTCTTACG (nt 571-592);

SEQ ID NO: 6
GATCATGGTGCTGGCGAAGTA (nt 978-958).

SEQ ID NO: 7
β-actin-
TGAAGTGTGACGTGGACATCCG (nt 96-117);

SEQ ID NO: 8
GCTGTCACCTTCACCGTT CCAG (nt 543-522).
```

Quantification of PCR products was performed by using a densitometer and a SCION IMAGE (Frederick, Md.) analysis, and/or PCR-ELISA.

PCR-ELISA: PCR was performed as described above except for the use of digoxigenin-labeled dNTPs. PCR products were incubated with biotinylated specific internal primers of the tested fragments that were immobilized in streptavidin-coated microtiter plates. The biotinylated internal primers served as capture probes. The bound digoxigenin-labeled PCR-products were then incubated with anti-digoxigenin-peroxidase conjugate that bound to the digoxigenin residues in the labeled PCR products. Peroxidase substrate solution was added, and the color developed was measured in a microtiter-plate reader.

Example 1

Table 1 summarizes the details (ages, sexes, and diagnoses) of schizophrenic patients and healthy controls from whom blood samples were obtained. RT-PCR was performed on total RNA preparations from these blood samples with primers specific for $D_3$ or $D_4$ dopamine receptor, and β-actin as a control. The specific PCR products were resolved on 2% agarose gels, and their sequences were verified. For each patient, a sex- and optimal age-matched healthy control was used, and the level of specific dopamine receptor mRNA was compared between sick and healthy patients. As depicted in FIG. 1 (a and b) for several representative patients, the signals for $D_3$ receptor mRNA were significantly higher in schizophrenic patients than in healthy controls. This increase was found to be specific for the $D_3$ dopamine receptor, because no significant differences in the intensities of $D_4$ receptor bands were detected between schizophrenic patients and healthy controls (FIGS. 1b, 1c).

Quantification of the intensities of the specific $D_3$ dopamine receptor bands was performed by densitometry. The results obtained for 13 patients are summarized in Table 2. Each schizophrenic patient was compared with a sex- and optimal age-matched healthy individual. For each of them, a ratio of the measured density value for $D_3$ receptor to the value for β-actin was determined. The ratio of these two values for a patient and a matched healthy control, respectively, represents the increased level (in folds) in $D_3$ specific mRNA in a given patient. As shown in Table 2, the increased levels obtained for the 13 patients range between 1.59 and 7.45 (mostly between 2-3). This increase in $D_3$ receptor mRNA in schizophrenic patients is significantly higher than the reported increases in binding levels and other recently suggested peripheral markers for schizophrenia (Avissar et al., 1997). Furthermore, the increase in $D_3$ receptor mRNA was not affected by different drug treatments. Although some of the patients received typical treatment and some atypical treatment (see Table 1), it can be noted that all patients exhibited a similar range of increase indicating that this was not a result of specific dopamine-receptor subtype blockade and up-regulation. Moreover, the present inventors found that this increase was not the consequence of a dopamine receptor antagonist treatment, because non-medicated patients (S12, S13) showed a similar increase in $D_3$ level (see Tables 1 and 2).

Another way to quantify the differences in a specific mRNA level was obtained from PCR-ELISA experiments (see Experimental part). Table 3 summarizes the results obtained from 6 patients. The increased mRNA levels observed are between 1.6 and 3.38 (average increase 2.30±0.63). It should be noted that there is a relatively good agreement between the quantitative values obtained by densitometry and by PCR-ELISA (see patients S1, S4 and S6 in Tables 2 and 3).

It should be added that the use of sex- and/or age-matched controls does not appear to be critical. The present inventors demonstrated that the differences in $D_3$ specific mRNA levels between schizophrenics and healthy individuals, determined by either densitometry or PCR-ELISA, were similar when compared with additional, not necessarily matched, controls (Table 4). This observation may be valuable in designing a practical assay wherein PBL from two or more healthy individuals may be pooled for use as a control.

In conclusion, these findings strongly suggest that $D_3$-receptor mRNA levels in PBLs may serve as a convenient and reliable peripheral marker for schizophrenia, thus assist in early diagnosis (which is frequently unclear), and possible follow-up of the illness.

Example 2

Thirty four patients were included in this study, 14 men and 20 women, ranging from 18 to 67 year of age. Of these, 20 were hospitalized schizophrenic patients, and 14 unmedicated patients that were examined during their first hospitalization. 21 healthy controls were studied, 11 nonsmokers and 10 smokers, 8 male and 13 female ranging from 31 to 62 years of age. Table 5 summarizes the details (age, sex and diagnosis) of schizophrenic patients and healthy controls participating in this study.

Figure 2:
FIG. 2 shows ethidium bromide staining of β-actin and α7 AChR PCR products obtained from mRNA of PBLs of schizophrenic (Sp) and control healthy (Hl) individuals.
Figure 2:
Figure 3:
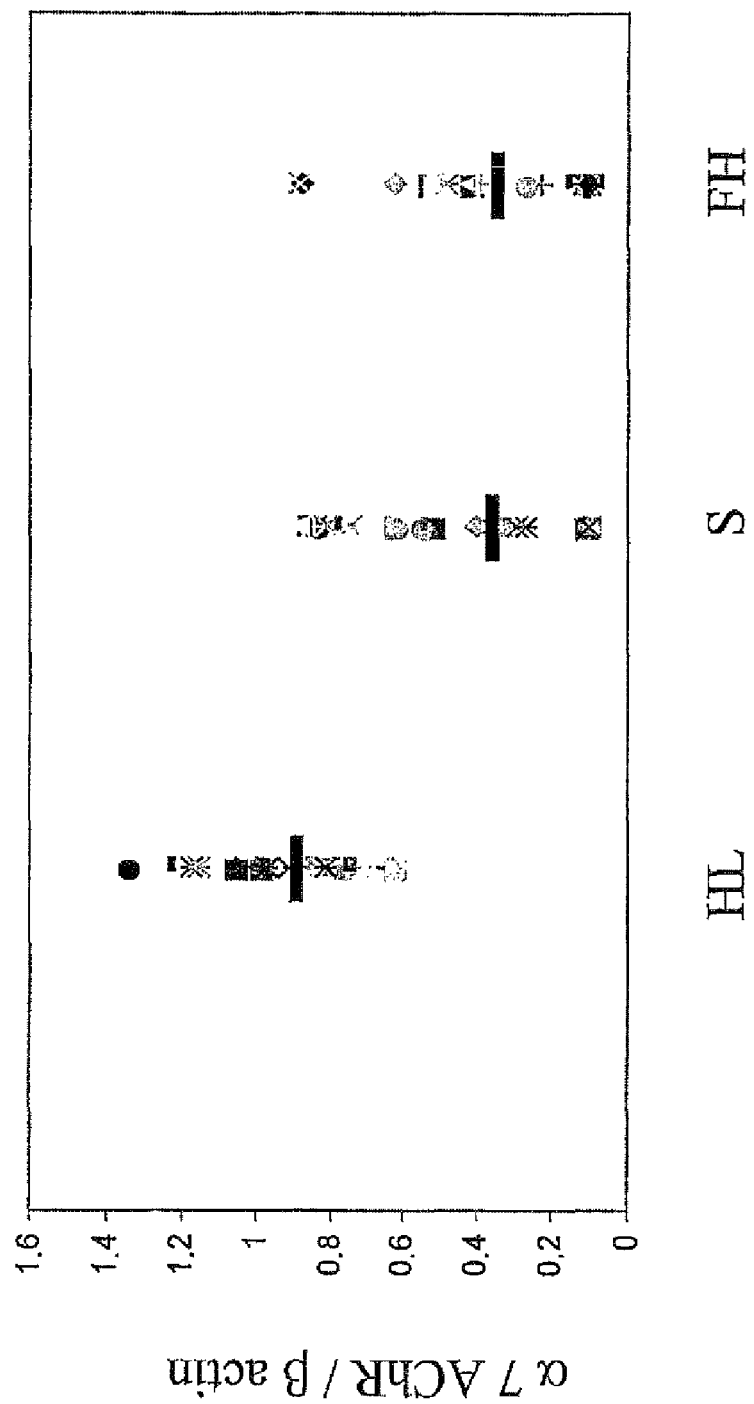
FIG. 3 shows a comparison of α7 AChR/β-actin mRNA ratios in PBLs of healthy controls (HL), schizophrenic patients (S) and unmedicated patients (tested in their first hospitalization, FH.

RNA was prepared from blood samples and RT-PCR was performed on total RNA, using specific primers for the α7 AChR, and for β-actin as a control. The specific PCR products were resolved on 1.5% agarose gels. As depicted in FIG. 2, the signals for α7 AChR were significantly lower in 3 schizophrenic patients than in 3 healthy controls. Quantification of the intensities of the specific α7 AChR and β-actin bands was performed by densitometry. The results obtained in 28 experiments are summarized in Table 6a. For each individual, a ratio of the measured density value for the α7 AChR to the value for β-actin was determined. Each patient was tested 1-4 times. As seen in Table 6a, 10 of the 34 tested patients had no detectable band for α7 AChR. The α7 AChR/β-actin ratios for these patients was arbitrarily determined as <0.1 (lower than the smallest calculated ratio in Table 6a). The α7 AChR/β-actin ratios for healthy controls (HL), schizophrenic patients (S) and unmedicated patients (first hospitalization, FH) obtained in all experiments are depicted in FIG. 3. The average values were 0.88±0.18, 0.36±0.30 and 0.34±0.26 for healthy controls, schizophrenic patients and unmedicated patients, respectively.

To determine the significance of the difference between healthy and schizophrenic patients, the α7 AChR/β-actin ratios obtained for 11 different healthy controls and for 14 different schizophrenic patients were compared by Sign test. In each experiment, the values obtained for the schizophrenic patients are significantly lower than for the corresponding healthy individuals (P<0.004).

The reduction in the level of α7 AChR mRNA observed in schizophrenic patients was calculated by the following equation: 100−100[(α7 AChR/β-actin S)/(α7 AChR/β-actin Hav)]. First, the average α7 AChR/β-actin ratios of all healthy controls in a given experiment was calculated (Hav). The decrease (%) of the α7 AChR mRNA for each patient was obtained after subtracting the % of (α7 AChR/β-actin S)/(α7 AChR/β-actin Hav) ratio from 100%. The % of decrease for all experiments were calculated, and are depicted in the last column of Table 6a. As seen in this Table, there were only 8 determinations (representing 6 different patients), in which the percent decrease was lower than 20%. All the other determinations in patients resulted in significant decreases in the α7 AChR mRNA levels, ranging from 20% to 98% decrease. So far, the present inventors have not observed a correlation between the percent decrease of α7 AChR mRNA and the disease state. However, it is interesting to point out that one unmedicated patient (FH2) that was tested in his first hospitalization, and exhibited a very low % decrease in its α7 AChR mRNA (5.1%, representing an average of three independent determinations), turned to be non schizophrenic following detailed psychiatric evaluation.

Figure 4:
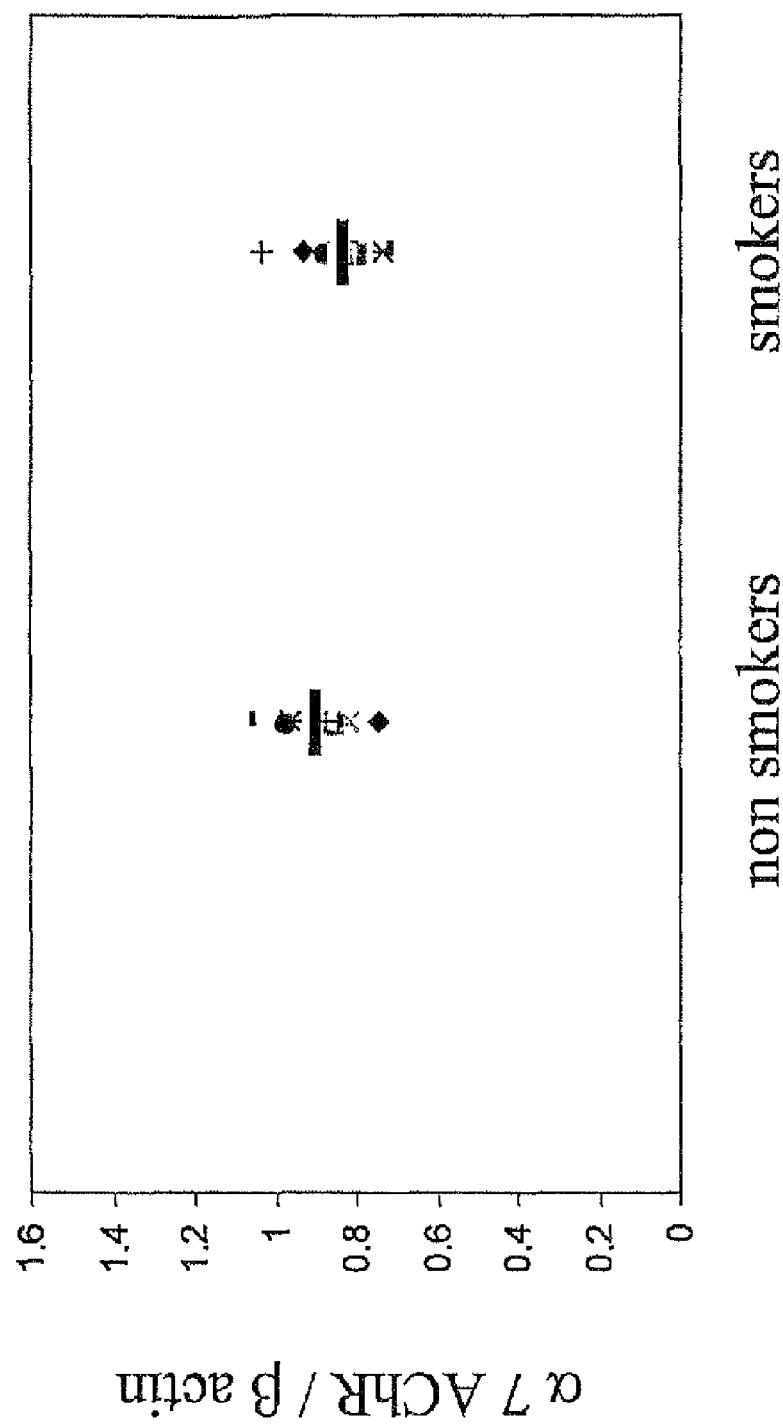
FIG. 4 shows a comparison of α7 AChR/β-actin mRNA ratios in PBL of healthy smokers and non-smokers.

The incidence of smoking in a mental illness, particularly in schizophrenia, is much higher than in the general population, 74-92% compared to 30-55%, respectively (Olincy et al., 1999). We have, therefore, tested whether smoking by itself has an effect on α7 AChR mRNA levels. Blood samples from healthy smokers that smoke a pack of cigarettes a day, and from healthy nonsmokers were analyzed for their α7 AChR mRNA levels. As depicted in Table 6b, there were no significant differences in the α7 AChR/β-actin ratios of smokers and nonsmokers. This suggests that the decrease in α7 AChR mRNA levels in schizophrenic patients is not a result of smoking. The α7 AChR/β-actin ratios for healthy smokers and nonsmokers are depicted in FIG. 4, demonstrating average ratios of 0.83±0.097 and 0.89±0.097, for smokers and nonsmokers, respectively.

The dopaminergic hypothesis of schizophrenia proposes that hyperactivity of dopamine transmission is responsible for the symptoms of this disorder. In the first example of the present invention we have demonstrated increased levels of $D_3$ dopamine receptor mRNA in PBLs of schizophrenic patients, when compared with the levels in healthy controls. In this example, the present inventors analyzed the mRNA levels of both $D_3$ dopamine receptor and of the α7 AChR in PBLs of a small group of patients. As expected, the levels of $D_3$ dopamine receptor mRNA were increased, whereas the levels of α7 AChR mRNA were decreased. As shown in Table 7, an increase of 55.52% in the levels of $D_3$ receptor mRNA and a decrease of 63.66% in the levels of α7 AChR mRNA were observed for patient SC8. The availability of two different biological markers (the mRNA level of $D_3$ dopamine receptor and α7 AChR) that can be both tested in PBLs makes the evaluation of schizoprenic patients by a peripheral and objective test, rather promising. Moreover, the fact that the mRNA level of these two receptor mRNAs changes in an opposite direction in schizophrenia, i.e., the gene expression of $D_3$ receptor increases, whereas the gene expression of α7 AChR decreases in PBLs of schizophrenic patients, that correlates with the changes in these receptors in the brain (as observed in post mortem schizophrenic patients), makes these assays experimentally convenient and reliable.

In conclusion, the decreased levels of mRNA of the α7 AChR in PBLs of schizophrenic patients, as presented herein, is consistent with earlier reports demonstrating a decrease in α7 AChR in post mortem brains of schizophrenic patients. Such correlation between decreased levels of α7 AChR mRNA in PBLs and the expression of schizophrenia justifies its application as a biological marker for this disease.

TABLE 1

Characterization of patients (Example 1).

Schizophrenic Patients:

| Number | Age | Sex | Diagnosis | Comments |
|---|---|---|---|---|
| S1 | 21 | M | Chronic negative schizophrenia | |
| S2 | 27 | M | Chronic negative schizophrenia | |
| S3 | 25 | M | Chronic negative schizophrenia | |
| S4 | 27 | F | Positive psychosis | |
| S5 | 49 | F | Acute schizophrenia | |
| S6 | 57 | F | Residual Schizophrenia | |
| S7 | 41 | M | Undifferentiated schizophrenia | |
| S8 | 54 | M | Paranoid schizophrenia | |
| S9 | 47 | M | Undifferentiated schizophrenia | |
| S10 | 42 | M | Undifferentiated schizophrenia | |
| S11 | 42 | M | Paranoid schizophrenia | |
| S12 | 21 | M | Undifferentiated schizophrenia | Non-medicated |
| S13 | 40 | F | Paranoid schizophrenia | Non-medicated |

Healthy Controls:

| Number | Age | Sex |
|---|---|---|
| C1 | 45 | F |
| C2 | 37 | F |
| C3 | 37 | M |
| C4 | 62 | F |
| C5 | 22 | M |
| C6 | 44 | M |
| C7 | 31 | M |
| C8 | 32 | M |
| C9 | 49 | F |
| C10 | 27 | M |
| C11 | 36 | F |

TABLE 2

Densitometric evaluation of $D_3$ and $D_4$ mRNA levels in patients as compared with their levels in healthy individuals. (Example 1)

A.

| | Schizophrenic patients: | | | Controls: | | | | $D_3$ fold increase (S/C) |
|---|---|---|---|---|---|---|---|---|
| Number | β-actin Arb. units | $D_3$ Arb. units | $D_3$/β-actin | Number | β-actin Arb. units | $D_3$ Arb. units | $D_3$/β-actin | |
| S1 | 67 | 51 | 0.671 | C3 | 86 | 23 | 0.267 | 2.513 |
| S2 | 87 | 56 | 0.643 | C3 | 86 | 23 | 0.267 | 2.408 |
| S3 | 82 | 60 | 0.731 | C3 | 86 | 23 | 0.267 | 2.737 |
| S4 | 98 | 100 | 1.02 | C2 | 95 | 61 | 0.642 | 1.588 |
| S5 | 55 | 143 | 2.600 | C2 | 58 | 59 | 1.017 | 2.556 |
| S6 | 75 | 153 | 2.040 | C4 | 79 | 70 | 0.886 | 2.302 |
| S7 | 19 | 171 | 9.000 | C10 | 85 | 163 | 1.917 | 4.694 |
| S8 | 138 | 426 | 3.087 | C8 | 425 | 176 | 0.414 | 7.456 |
| S9 | 89 | 60 | 0.674 | C7 | 121 | 28 | 0.231 | 2.917 |
| S10 | 107 | 71 | 0.663 | C7 | 121 | 28 | 0.231 | 2.870 |
| S11 | 303 | 277 | 0.914 | C3 | 271 | 29 | 0.107 | 6.644 |
| S12 | 319 | 227 | 0.711 | C7 | 273 | 86 | 0.315 | 2.257 |
| S13 | 237 | 354 | 1.493 | C9 | 199 | 130 | 0.653 | 2.870 |

B.

| | Schizophrenic patients: | | | Controls: | | | $D_4$ fold increase (S/C) |
|---|---|---|---|---|---|---|---|
| Number | β-actin Arb. units | $D_4$ Arb. units | $D_4$/β-actin | Number | β-actin Arb. units | $D_4$ Arb. units | $D_4$/β-actin | |
| S1 | 74 | 70 | 0.945 | C3 | 67 | 70 | 1.044 | 0.905 |
| S2 | 71 | 72 | 1.010 | C3 | 67 | 70 | 1.044 | 0.967 |
| S3 | 72 | 74 | 1.027 | C3 | 67 | 70 | 1.044 | 0.983 |
| S4 | 67 | 71 | 1.059 | C2 | 82 | 73 | 0.890 | 1.189 |

TABLE 3

Evaluation by PCR-ELISA of D3 mRNA levels in patients as compared with their levels in healthy individuals. (Example 1)

| | Schizophrenic patients: | | | | Controls: | | | $D_3$ fold increase (S/C) |
|---|---|---|---|---|---|---|---|---|
| Number | β-actin (O.D) | $D_3$ (O.D) | $D_3$/β-actin | Number | β-actin (O.D) | $D_3$ (O.D) | $D_3$/β-actin | |
| S1 | 0.556 | 0.868 | 1.56 | C8 | 0.918 | 0.552 | 0.601 | 2.595 |
| S2 | 0.808 | 2.225 | 2.75 | C9 | 0.405 | 0.33 | 0.814 | 3.378 |
| S3 | 0.224 | 0.253 | 1.13 | C8 | 0.533 | 0.272 | 0.510 | 2.215 |
| S4 | 0.629 | 0.394 | 0.626 | C8 | 0.876 | 0.316 | 0.360 | 1.738 |
| S5 | 0.340 | 0.823 | 2.420 | C2 | 0.365 | 0.533 | 1.46 | 1.657 |
| S6 | 0.339 | 0.899 | 2.652 | C3 | 0.368 | 0.444 | 1.206 | 2.199 |

TABLE 4

Evaluation of $D_3$ mRNA levels in patients as compared with their levels in several healthy individuals (Example 1)

| Schizophrenia patients: | | Controls: | | |
|---|---|---|---|---|
| Number | | Number | $D_3$/β-actin | Ratio |
| S8 | 3.087 | C8 | 0.414 | 7.456 |
| | | C9 | 0.498 | 6.198 |
| S5 | 2.600 | C2 | 1.017 | 2.6 |
| | | C3 | 1.145 | 2.27 |
| | | C4 | 0.886 | 2.934 |
| S6 | 2.040 | C2 | 1.017 | 2.005 |
| | | C3 | 1.145 | 1.78 |
| | | C4 | 0.886 | 2.302 |
| S4 | 1.02 | C2 | 0.642 | 1.588 |
| | | C8 | 0.656 | 1.554 |

TABLE 5

Characteristics of patients and healthy donors (Example 2)

| Sample | Age | Gender | Diagnosis |
|---|---|---|---|
| Healthy controls (nonsmokers) | | | |
| HL16 | 49 | F | |
| HL15 | 32 | M | |
| HL14 | 31 | M | |
| HL10 | 37 | M | |
| HL5 | 40 | M | |
| HL9 | 39 | F | |
| HL18 | 36 | F | |
| HL11 | 62 | F | |
| HL6 | 35 | M | |
| HL19 | 32 | M | |
| HL20 | 35 | F | |
| Healthy smokers | | | |
| SM1 | 52 | F | |
| SM2 | 35 | M | |
| SM3 | 35 | F | |
| SM4 | 41 | M | |
| SM6 | 44 | F | |
| SM7 | 37 | F | |
| SM8 | 45 | F | |
| SM9 | 54 | F | |
| SM10 | 55 | F | |
| SM11 | 50 | F | |
| Schizophrenic patients | | | |
| SP1 | 21 | M | Schizophrenia-residual type |
| SP2 | 27 | M | Schizophrenia-paranoid type |

TABLE 5-continued

Characteristics of patients and healthy donors (Example 2)

| Sample | Age | Gender | Diagnosis |
|---|---|---|---|
| SP3 | 25 | M | Schizophrenia-undifferentiated type |
| SP7 | 49 | F | Schizophrenia-paranoid type |
| SP8 | 57 | F | Schizophrenia-residual type |
| SP9 | 31 | F | Schizophrenia-paranoid type |
| SP12 | 56 | F | Schizophrenia-undifferentiated type |
| SP13 | 54 | M | Schizophrenia-paranoid type |
| SP15 | 31 | F | Schizophrenia-paranoid type |
| SP19 | 54 | F | Schizophrenia-paranoid type |
| SP20 | 45 | F | Schizophrenia |
| BY8 | 39 | M | Schizophrenia-residual type |
| BY9 | 62 | F | Disorganized Schizophrenia |
| BY10 | 67 | F | Disorganized Schizophrenia |
| BY11 | 50 | M | Schizophrenia |
| SC6 | 51 | M | Schizophrenia |
| SC7 | 24 | F | Schizophrenia |
| SC8 | 64 | F | Schizophrenia |
| SC10 | 63 | F | Schizophrenia |
| SP5 | 65 | F | Schizophrenia-undifferentiated type |
| Schizophrenic patients (First hospitalization) | | | |
| BY14 | 40 | F | Schizophrenia-paranoid type |
| FH2 | 30 | F | |
| FH3 | 27 | M | Personality disorder |
| FH4 | 40 | M | Psychotic episode |
| FH5 | 18 | M | Schizophrenia |
| FH6 | 21 | M | Personality disorder |
| FH7 | 26 | M | Acute psychotic disorder |
| FH9 | 26 | F | Schizophrenia-moderately ill |
| FH10 | 23 | F | Schizophrenia-markedly ill |
| FH11 | 20 | F | Schizophrenia-moderately ill |
| FH12 | 35 | M | Acute psychotic disorder |
| FH13 | 38 | M | Schizophrenia-moderately ill |
| FH14 | 20 | F | Acute psychotic disorder |
| FH15 | 48 | F | Acute psychotic disorder |

TABLE 6a

Evaluation of α7/β-actin mRNA levels of schizophrenic patients compared to healthy controls (Example 2)

| Exp. No. | Sample No. | Schizophrenic patients β-actin (arb. Units) | α7 (arb. Units) | α7/β-actin | Sample No. | Healthy controls β-actin (arb. Units) | α7 (arb. Units) | α7/β-actin | Decrease % |
|---|---|---|---|---|---|---|---|---|---|
| 1 | SP1 | 206.49 | 75.77 | .37 | HL16 | 228.25 | 223.65 | .98 | 59.99 |
|  | SP2 | 220.25 | 109.33 | .496 | HL15 | 235.74 | 230.62 | .99 | 45.87 |
|  | SP3 | 215.3 | 91.46 | .42 | HL14 | 206.45 | 163.76 | .79 | 53.68 |
| 2 | SP7 | 155.53 | 134.14 | .86 | HL16 | 166.3 | 152.18 | .92 | 17.35 |
|  | SP8 | 168.35 | 140.64 | .84 | HL5 | 131.47 | 154.08 | 1.17 | 19.95 |
|  | SP9 | 135.95 | 112.06 | .82 |  |  |  |  | 21.01 |
| 3 | SP3 | 133.48 | 118.31 | .89 | HL16 | 104.04 | 138.75 | 1.33 | 23.08 |
|  | SP12 | 143.23 | 123.66 | .86 | HL15 | 130.7 | 118.01 | .90 | 25.07 |
|  |  |  |  |  | HL14 | 106.07 | 129.44 | 1.22 |  |
| 4 | SP19 | 173.83 | 93.35 | .54 | HL14 | 175.14 | 138.94 | .79 | 41.15 |
|  | SP15 | 159.95 | undetectable | <0.1 | HL19 | 175.91 | 164.57 | .94 | >89.05 |
|  |  |  |  |  | HL16 | 164.39 | 165.8 | 1.01 |  |
| 5 | BY8 | 108.54 | 80.63 | .74 | HL16 | 114.12 | 131.7 | 1.15 | 35.63 |
|  | BY10 | 97.75 | undetectable | <0.1 |  |  |  |  | >91.31 |
|  | BY11 | 101.5 | undetectable | <0.1 |  |  |  |  | >91.31 |
| 6 | BY14 | 182.8 | 114 | .62 | HL18 | 181.07 | 128.85 | .69 | 10.27 |
| 7 | FH2 | 221.62 | 188.4 | .85 | HL18 | 241.88 | 210.59 | .87 | 3.97 |
|  | SP19 | 228.01 | 138.64 | .61 | HL15 | 236.86 | 194.03 | .82 | 31.31 |
|  | SP20 | 171.5 | undetectable | <0.1 | HL11 | 235.08 | 227.08 | .97 | >88.72 |
|  | SP3 | 202.13 | undetectable | <0.1 |  |  |  |  | >88.72 |
|  | BY10 | 240.7 | 179.56 | .75 |  |  |  |  | 15.73 |
| 8 | SC7 | 170.88 | 144.4 | .85 | HL6 | 148.91 | 144.1 | .97 | 12.68 |
|  | SC10 | 124.7 | 95.67 | .77 |  |  |  |  | 20.72 |
|  | FH6 | 162.22 | undetectable | <0.1 |  |  |  |  | >90.30 |
|  | SC6 | 158.41 | undetectable | <0.1 |  |  |  |  | >90.30 |
| 9 | SC7 | 201.25 | 127.85 | .64 | HL6 | 187.14 | 157.69 | .84 | 24.61 |
|  | SC10 | 215.77 | 86.5 | .40 |  |  |  |  | 52.42 |
|  | FH6 | 201.53 | 81.66 | .41 |  |  |  |  | 51.91 |
|  | FH7 | 165.53 | 68.99 | .42 |  |  |  |  | 50.54 |
|  | SC6 | 180.86 | undetectable | <0.1 |  |  |  |  | >88.10 |
|  | SC8 | 209.27 | undetectable | <0.1 |  |  |  |  | >88.10 |
| 10 | FH2 | 227.06 | 199.01 | .88 | HL11 | 229.63 | 170.67 | 0.74 | −9.80 |
|  |  |  |  |  | HL14 | 239.21 | 204.11 | 0.85 |  |
| 11 | SP3 | 190.77 | 51.58 | .27 | HL9 | 190.34 | 123.79 | .65 | 58.43 |
| 12 | SP1 | 166.62 | 90.67 | .54 | HL5 | 155.5 | 100.14 | .64 | 41.36 |
|  | SP2 | 167.84 | 90 | .54 | HL9 | 164.2 | 103.37 | .63 | 42.22 |
|  | SP3 | 157.41 | undetectable | <0.1 | HL9 | 167.36 | 102.55 | .61 | >85.62 |
|  | SP20 | 145.1 | undetectable | <0.1 | HL14 | 167.28 | 150.2 | .90 | >85.62 |
| 13 | SP15 | 126.61 | undetectable | <0.1 | HL10 | 154.99 | 85.57 | 0.55 | >81.31 |
|  |  |  |  |  | HL9 | 145.48 | 74.96 | 0.52 |  |
| 14 | SP3 | 186.89 | undetectable | <0.1 | HL9 | 177.55 | 137.62 | 0.78 | >86.85 |
|  | SP15 | 166.82 | undetectable | <0.1 | HL10 | 170.43 | 139.54 | 0.82 | >86.85 |
|  | SP19 | 181.28 | undetectable | <0.1 | HL15 | 170.05 | 100.22 | 0.59 | >86.85 |
| 15 | SP9 | 166.45 | undetectable | <0.1 | HL15 | 168.02 | 90.39 | 0.54 | >80.59 |
|  | SP19 | 139.61 | undetectable | <0.1 | HL16 | 168.81 | 91.01 | 0.54 | >80.59 |
|  |  |  |  |  | HL10 | 166.02 | 81.96 | 0.49 |  |
|  |  |  |  |  | HL18 | 168.06 | 82.67 | 0.49 |  |
| 16 | SP19 | 220.14 | undetectable | <0.1 | HL14 | 217.55 | 131.95 | 0.61 | >85.30 |
|  | SP20 | 197.13 | undetectable | <0.1 | HL5 | 203.7 | 153.4 | 0.75 | >85.30 |
| 17 | SP15 | 179.26 | undetectable | <0.1 | HL9 | 209.93 | 146.15 | 0.70 | >85.72 |
| 18 | FH2 | 61.84 | 26.08 | 0.52 | HL18 | 76.29 | 46.87 | 0.61 | 21.94 |
|  | FH3 | 54.38 | 4.93 | 0.11 | HL11 | 72.83 | 52.98 | 0.73 | 83.00 |
| 19 | FH3 | 63.37 | 6.54 | 0.10 | HL5 | 29.82 | 14.75 | 0.49 | 74.90 |
|  | SP9 | 52.77 | undetectable | <0.1 |  |  |  |  | >79.60 |
|  | SP5 | 32.03 | undetectable | <0.1 |  |  |  |  | >79.60 |
|  | SP12 | 45.16 | undetectable | <0.1 |  |  |  |  | >79.60 |
|  | SP13 | 20.1 | undetectable | <0.1 |  |  |  |  | >79.60 |
|  | FH4 | 60.35 | undetectable | <0.1 |  |  |  |  | >79.60 |
| 20 | FH7 | 43.61 | 10 | 0.23 | SM7 | 95.28 | 55.89 | 0.59 | 65.26 |
|  | FH9 | 99.78 | 14.48 | 0.15 | SM8 | 105.05 | 72.68 | 0.69 | 78.01 |
|  | FH5 | 81.75 | undetectable | <0.1 | SM9 | 84.78 | 49.92 | 0.59 | >84.85 |
|  |  |  |  |  | SM10 | 89 | 68.77 | 0.77 |  |
| 21 | FH9 | 92.99 | 50.54 | 0.54 | SM9 | 81.75 | 69.1 | 0.85 | 35.70 |
|  | FH7 | 94.76 | undetectable | <0.1 |  |  |  |  | >88.24 |
|  | SC6 | 79.03 | undetectable | <0.1 |  |  |  |  | >88.24 |
| 22 | FH9 | 63.85 | 32.77 | 0.51 | SM9 | 63.48 | 50.93 | 0.80 | 36.03 |
|  | FH7 | 53.35 | undetectable | <0.1 |  |  |  |  | >87.5 |
| 23 | SC8 | 66.84 | 6.25 | 0.09 | C3 | 84.21 | 17.32 | 0.21 | 54.54 |
|  | SC6 | 39.87 | undetectable | <0.1 |  |  |  |  | >52.39 |
| 24 | FH9 | 92.3 | 47.22 | 0.51 | H2 | 127.12 | 111.29 | 0.88 | 46.85 |
|  | FH10 | 66.85 | undetectable | <0.1 | HL6 | 127.53 | 133.84 | 1.05 | >89.64 |

TABLE 6a-continued

Evaluation of α7/β-actin mRNA levels of schizophrenic patients compared to healthy controls (Example 2)

| | | Schizophrenic patients | | | | Healthy controls | | | |
|---|---|---|---|---|---|---|---|---|---|
| Exp. No. | Sample No. | β-actin (arb. Units) | α7 (arb. Units) | α7/β-actin | Sample No. | β-actin (arb. Units) | α7 (arb. Units) | α7/β-actin | Decrease % |
| 25 | FH11 | 95.22 | 76.43 | 0.80 | C3 | 99.08 | 103.75 | 1.05 | 23.35 |
| | FH12 | 101.4 | 92.47 | 0.91 | | | | | 12.91 |
| | FH13 | 93.01 | 82.36 | 0.89 | | | | | 15.44 |
| | FH14 | 72.02 | 34.75 | 0.48 | | | | | 53.92 |
| | FH15 | 101.95 | 26.55 | 0.26 | | | | | 75.13 |
| 26 | FH15 | 108.85 | 38.52 | 0.35 | C3 | 120.6 | 119.12 | 0.99 | 64.17 |
| | FH14 | 95.75 | undetectable | <0.1 | | | | | >89.9 |
| 27 | SC8 | 67.04 | 0.75 | 0.01 | C3 | 71.26 | 64.85 | 0.91 | 98.78 |
| | FH14 | 47.29 | 3.21 | 0.07 | | | | | 92.54 |
| | FH15 | 74.17 | 29.25 | 0.39 | | | | | 56.67 |
| 28 | BY9 | 212.5 | 94.95 | 0.45 | HL18 | 187.8 | 114.39 | 0.61 | 35.71 |

TABLE 6b

Evaluation of α7/β-actin mRNA levels of smokers compared to non smokers (Example 2)

| | | Smokers (healthy controls) | | | | Non smokers (healthy controls) | | | |
|---|---|---|---|---|---|---|---|---|---|
| Exp No. | Sample No. | β-actin (arb. Units) | α7 (arb. Units) | α7/β-actin | Sample No. | β-actin (arb. Units) | α7 (arb. Units) | α7/β-actin | Decrease % |
| 1 | SM1 | 245.51 | 228.35 | .93 | HL11 | 229.63 | 170.67 | 0.74 | −16.52 |
| | SM3 | 235.09 | 187.18 | .80 | HL14 | 239.21 | 204.11 | 0.85 | .26 |
| | SM4 | 228.96 | 192.34 | .84 | | | | | −5.24 |
| 2 | SM6 | 148.88 | 125.74 | .84 | HL6 | 148.91 | 144.1 | .97 | 12.72 |
| | SM7 | 170.86 | 125.14 | .73 | | | | | 24.31 |
| | SM8 | 170.29 | 149.14 | .88 | | | | | 9.50 |
| 3 | SM7 | 216.7 | 223.81 | 1.03 | HL6 | 187.14 | 157.69 | .84 | −22.57 |
| | SM8 | 165.87 | 117.62 | .71 | | | | | 15.85 |
| 4 | SM1 | 240.84 | 202.56 | 0.84 | HL18 | 241.88 | 210.59 | .87 | 4.99 |
| | | | | | HL15 | 236.86 | 194.03 | .82 | |
| | | | | | HL11 | 235.08 | 227.08 | .97 | |

TABLE 7

Comparison of α7 and $D_3$ mRNA levels

| Sample | β-actin (arb. Units) | α7 (arb. Units) | α7/β-actin | Decrease % | Fold | β-actin (arb. Units) | D3 (arb. Units) | D3/β-actin | Increase % | Fold |
|---|---|---|---|---|---|---|---|---|---|---|
| C3 | 83.36 | 67.28 | 0.81 | | | 83.36 | 0.65 | 0.007 | | |
| SC8 | 67.31 | 19.86 | 0.30 | 63.66 | 2.7 | 67.31 | 1.18 | 0.02 | 55.52 | 2.86 |

REFERENCES

Avissar, S., Nechamkin, Y., Barki-Harrington, L., Roitman, G, and Schreiber, G. 1997. Differential G protein measures in mononuclear leukocytes of patients with bipolar mood disorder are state dependent. Affect Disord 43:85.

Bondy, B., Ackenheil, M., Birzle, W., Elbers, R, and Frohler, M. 1984. Catecholamines and their receptors in blood: evidence for alterations in schizophrenia. Biol Psychiatry 19:1377.

Bondy, B., Ackenheil, M., Elbers, R, and Frohler, M. 1985. Binding of 3H-spiperone to human lymphocytes: a biological marker in schizophrenia? Psychiatry Res 15:41.

Burghaus, L., Aschutz, U., Krempel, U., Rob A. I. de Vos, Ernst N. H. Steur, J., Wevers, A., Lindstrom, J., and Hannsjorg. 2000. Quantitative assessment of nicotinic acetylcholine receptor proteins in the cerebral cortex of Alzheimer patients. Mol. Brain Research 76: 385-388.

Court J., Spurden D., Lloyd S., McKeith I., Ballard C., Cairns N., Kerwin R., Perry R., and Perry E. 1999. Neuronal nicotinic receptors in dementia with Lewy bodies and schizophrenia: alpha-bungarotoxin and nicotine binding in the thalamus. J. Neurochem. October; 73(4): 1590-7.

Creese, I., Burt, D. R, and Snyder, S. H. 1976. dopamine receptor binding predicts clinical and pharmacological potencies of antischizophrenic drugs. Science 192:481.

Ferrero, P., Rocca, P., Eva, C., Benna, P., Rebaudengo, N., Ravizza, L., Genazzani, E, and Bergamasco, B. 1991. An analysis of lymphocyte 3H-N-methyl-scopolamine binding in neurological patients. Brain 114:1759.

Freedman, R., Adams, C. E., and Leonard, S. 2000. The α7-nicotinic acetylcholine receptor and the pathology of hippocampal interneurons in schizophrenia. J. of Chem. Neuroanatomy 20: 299-306.

Grodzicki, J., Pardo, M., Schved, G., Schlosberg, A., Fuchs, S, and Kanety, H. 1990. Differences in [3H]-spiperone binding to peripheral blood lymphocytes from neuroleptic responsive and nonresponsive schizophrenic patients. Biol Psychiatry 27:1327.

Guan, Z., Zhang, X., Blennow, K., and Nordberg, A. 1999. Decreased protein level of nicotinic receptor α7 subunit in the frontal cortex from schizophrenic brain. Neuro. Report 10: 1779-1782.

Guan, Z., Zhang, X., Ravid, R., and Nordberg, A. 2000. Decreased protein levels of nicotinic receptor subunits in the hippocampus and temporal cortex of patients with Alzheimer's disease. J. of Neurochem. 74:237-243.

Hellstrom-Lindahl, E., Zhang, X., and Nordberg, A. 1997. Expression of nicotinic receptor subunit mRNAs in lymphocytes from normal and patients with Alzheimer's disease. Alz. Research 3:29-36.

Hellstrom-Lindahl, E., Mousavi, M., Zhang, X., Ravid, R., and Nordberg, A. 1999. Regional distribution of nicotinic receptor subunit mRNAs in human brain: comparison between Alzheimer and normal brain. Mol. Brain Research 66:94-103.

Hietala, J, and Syvalahti, E. 1996. Dopamine in schizophrenia. Ann Med 28:557.

Karlsson, P., Farde, S. L., Harnryd, G. S, and Wiesel, F. A. 1995. Lack of apparent antipsychotic effect of D1-dopamine receptor antagonist SCH39166 in acutely ill schizophrenic patients. Psychopharmacology 121:309.

Leonard, S., Breese, C., Adams, C., Benhammou, K., Gault, J., Stevens, K., Lee, M., Adler, L., Olincy, A., Ross, R., and Freedman, R. 2000. Smoking and schizophrenia: abnormal nicotinic receptor expression. European Journal of Pharmacology 393: 237-242.

Levant, B. 1997. The D3 dopamine receptor: neurobiology and potential clinical relevance. Pharmacol Rev 49:231.

Nagai, Y., Ueno, S., Saeki, Y., Soga, F., Hirano, M, and Yanagihara, T. 1996. Decrease of the D3 dopamine receptor mRNA expression in lymphocytes from patients with Parkinson's disease. Neurology 46:791. responsive and nonresponsive schizophrenic patients. Biol Psychiatry 27:1327.

Olincy, A., Leonard, S., Young, D. A., Sullivan, B., and Freedman, R. 1999. Decreased bombesin peptide response to cigarette smoking in schizophrenia. Neuropsychopharmacology Vol 20(1): 52-59.

Olincy, A., Ross, R. G., Young, D. A., Roath, M., and Freedman R. 1998. Improvement in smooth pursuit eye movements after cigarette smoking in schizophrenic patients. Neuropsychopharmacology Vol 18:175-185.

Olincy, A., Young, DA., Freedman, R. 1997. Increased levels of the nicotine metabolite cotinine in schizophrenia compared to other smokers. Biol. Psychiatry July 1; 42(1):1-5.

Ricci, A., Bronzetti, E., Felici, L., Tayebati, S. K, and Amenta, F. 1997 Dopamine D4 receptor in human peripheral blood lymphocytes: a radioligand binding assay study. Neurosci Lett 229:130.

Seeman, P, and Niznik, H. B. 1990. Dopamine receptors and transporters in Parkinson's disease and schizophrenia. FASEB J 4:2737.

Stassen, H. H., Bridler, R., Hagele, S., Hergersberg, S., Mehmann, B., Schinzel, A., Weisbrod, M., and Scharfetter., C. 2000. Schizophrenia and smoking: Evidence for a common neurobiological basis? American J. of Med. Gen. 96:173-177.

Takahashi, N., Nagai, Y., Ueno, S., Saeki Y, and Yanagihara, T. 1992. Human peripheral blood lymphocytes express D5 dopamine receptor gene and transcribe the two pseudogenes. FEBS Lett 314:23.

Wang, H Y., Lee, D H., D'Andrea, M R., Peterson, P A., Shank, R P., Reitz, A B. 2000. Beta-amyloid (1-42) binds to alpha-7 nicotinic acetylcholine receptor with high affinity. Implications for Alzheimer's disease pathology. J. Biol. Chem. 275 (8):5626-32.

Willner, P. 1997. The dopamine hypothesis of schizophrenia: current status, future prospects. Int Clin Psychopharmacol 12:297.

---

The invention claimed is:

1. A method for diagnosing the likelihood of schizophrenia in a tested individual, comprising:
   (i) measuring mRNA of D3 dopamine receptor and of a control gene in peripheral blood lymphocytes (PBLs) of said tested individual and of a pool of two or more healthy individuals;
   (ii) calculating the ratio between the D3 dopamine receptor mRNA and the control gene mRNA for the tested individual and the pool of two or more healthy individuals; and
   (iii) comparing the ratios obtained in (ii) for the tested individual and for the pool of two or more healthy individuals, wherein an increase of above 1.6-fold in the D3 dopamine receptor mRNA/control gene mRNA ratio in the tested individual, in comparison to that of the pool of two or more healthy individuals, indicates that said tested individual has a higher likelihood of having schizophrenia than said healthy individuals.

2. A method according to claim 1, wherein the mRNA of D3 dopamine receptor and of the control gene in step (i) is measured by reverse transcription-polymerase chain reaction (RT-PCR).

3. A method according to claim 1, wherein the control gene is β-actin.

4. A method according to claim 1, wherein an increase of the D3 dopamine receptor mRNA/control gene mRNA ratio evaluated in step (iii) in the tested individual of 2-4 folds, in comparison to that of the pool of two or more healthy individuals, serves as the indicator that the tested individual has a likelihood of having schizophrenia.

5. A method according to claim 1, wherein the tested individual is non-medicated.

6. A method for diagnosing the likelihood of schizophrenia in a tested individual, comprising:
   (i) measuring mRNA of α7 nicotinic acetylcholine receptor (α7 AChR) and of a control gene in peripheral blood lymphocytes (PBLs) of said tested individual and of a pool of two or more healthy individuals;

(ii) calculating the ratio between α7 AChR mRNA and the control gene mRNA for the tested individual and the pool of two or more healthy individuals; and (iii) comparing the ratios obtained in (ii) for the tested individual and for the pool of two or more healthy individuals, wherein a decrease of more than 20% in the α7 AChR mRNA/control gene mRNA ratio in the tested individual, in comparison to that of the pool of two or more healthy individuals, indicates that said tested individual has a higher likelihood of having schizophrenia than said healthy individuals.

7. A method according to claim 6, wherein the mRNA of α7 AChR and of the control gene in step (i) is measured by reverse transcription-polymerase chain reaction (RT-PCR).

8. A method according to claim 6, wherein the control gene is β-actin.

9. A method according to claim 6, wherein a decrease of the α7 AChR mRNA/control gene mRNA ratio evaluated in step (iii) in the tested individual of 20-98%, in comparison to that of the pool of two or more healthy individuals, serves as the indicator that the tested individual has a likelihood of having schizophrenia.

10. A method according to claim 6, wherein the tested individual is non-medicated.

* * * * *